(12) United States Patent
Pillarisetty et al.

(10) Patent No.: US 11,450,416 B2
(45) Date of Patent: Sep. 20, 2022

(54) LOCATION-BASED HEALTHCARE SYSTEM

(71) Applicant: CERNER INNOVATION, INC., Kansas City, KS (US)

(72) Inventors: Satya Krishna Pillarisetty, Bangalore (IN); Krishna Kumar, Bangalore (IN); Mahesh Vilas Kotekar, Bangalore (IN); Pradeep Premakumar, Bangalore (IN); Thampuraj Dharmamoorthy, Bangalore (IN)

(73) Assignee: CERNER INNOVATION, INC., North Kansas City, MO (US)

( * ) Notice: Subject to any disclaimer, the term of this patent is extended or adjusted under 35 U.S.C. 154(b) by 594 days.

(21) Appl. No.: 15/391,552

(22) Filed: Dec. 27, 2016

(65) Prior Publication Data

US 2018/0181713 A1 Jun. 28, 2018

(51) Int. Cl.
*G16H 10/60* (2018.01)
*G16H 50/30* (2018.01)
(Continued)

(52) U.S. Cl.
CPC ............. *G16H 10/60* (2018.01); *G16H 40/67* (2018.01); *G16H 50/30* (2018.01); *G16H 50/80* (2018.01)

(58) Field of Classification Search
CPC ........ G06Q 30/00; G06Q 50/22; G06Q 30/06; G06Q 10/1097; G06Q 30/02; G06Q 50/01;
(Continued)

(56) References Cited

U.S. PATENT DOCUMENTS 7,860,725 B2 12/2010 Gopinathan et al.
2006/0036619 A1* 2/2006 Fuerst et al.
(Continued)

FOREIGN PATENT DOCUMENTS

WO 2006/039944 A1 4/2006

OTHER PUBLICATIONS

Final Office Action received for U.S. Appl. No. 15/392,720, dated Dec. 23, 2019, 19 pages.
(Continued)

*Primary Examiner* — Michael Tomaszewski
*Assistant Examiner* — William T. Monticello
(74) *Attorney, Agent, or Firm* — Shook, Hardy & Bacon L.L.P.

(57) ABSTRACT

A computerized method is presented for communicating an alert to an individual of a medical-related risk and storing in the individual's healthcare records information related to the individual's exposure to the medical-related risk. The method comprises constantly monitoring the individual's location; receiving an environmental report from a service provider containing current environmental factors, where the report is associated with an area; determining that the individual is within or proximate to the area associated with the report; retrieving medical records for the individual; determining, according to the medical records, that the environmental factors pose a medical-related risk to the individual; communicating the alert to the individual of the medical-related risk associated with the area; determining the individual was exposed to the medical-related risk; storing in the individual's healthcare records information related to the exposure. The methods may also comprise recommending orders, based on the exposure, for a medical professional to write.

19 Claims, 6 Drawing Sheets

(51) Int. Cl.
*G16H 40/67* (2018.01)
*G16H 50/80* (2018.01)

(58) Field of Classification Search
CPC ........ G06Q 50/00; G06Q 40/00; G06H 10/60;
G06F 19/3418; G06F 17/00; G05B 15/02;
H04R 3/00; H04L 12/2827; G16H 50/30
See application file for complete search history.

(56) References Cited

U.S. PATENT DOCUMENTS

| | | |
|---|---|---|
| 2007/0118399 A1* | 5/2007 | Avinash et al. |
| 2011/0093249 A1* | 4/2011 | Holmes et al. |
| 2012/0084092 A1* | 4/2012 | Kozuch et al. |
| 2012/0158431 A1 | 6/2012 | Balasubramaniam |
| 2016/0019813 A1* | 1/2016 | Mullen |
| 2016/0071432 A1* | 3/2016 | Kurowski et al. |
| 2016/0321395 A1 | 11/2016 | Colby et al. |
| 2017/0199979 A1* | 7/2017 | Reiner |
| 2017/0242970 A1* | 8/2017 | Fink et al. |
| 2017/0286622 A1* | 10/2017 | Cox et al. |
| 2018/0052970 A1* | 2/2018 | Boss et al. |
| 2018/0089976 A1* | 3/2018 | Yarlagadda et al. |
| 2018/0101655 A1* | 4/2018 | Fogelberg et al. |
| 2018/0101657 A1* | 4/2018 | Kochura et al. |
| 2018/0144092 A1* | 5/2018 | Flitsch et al. |

OTHER PUBLICATIONS

Non-Final Office Action received for U.S. Appl. No. 15/392,720, dated Oct. 6, 2020, 21 pages.
Notice of Allowance received for U.S. Appl. No. 15/392,720, dated Jul. 22, 2021, 10pages.

* cited by examiner

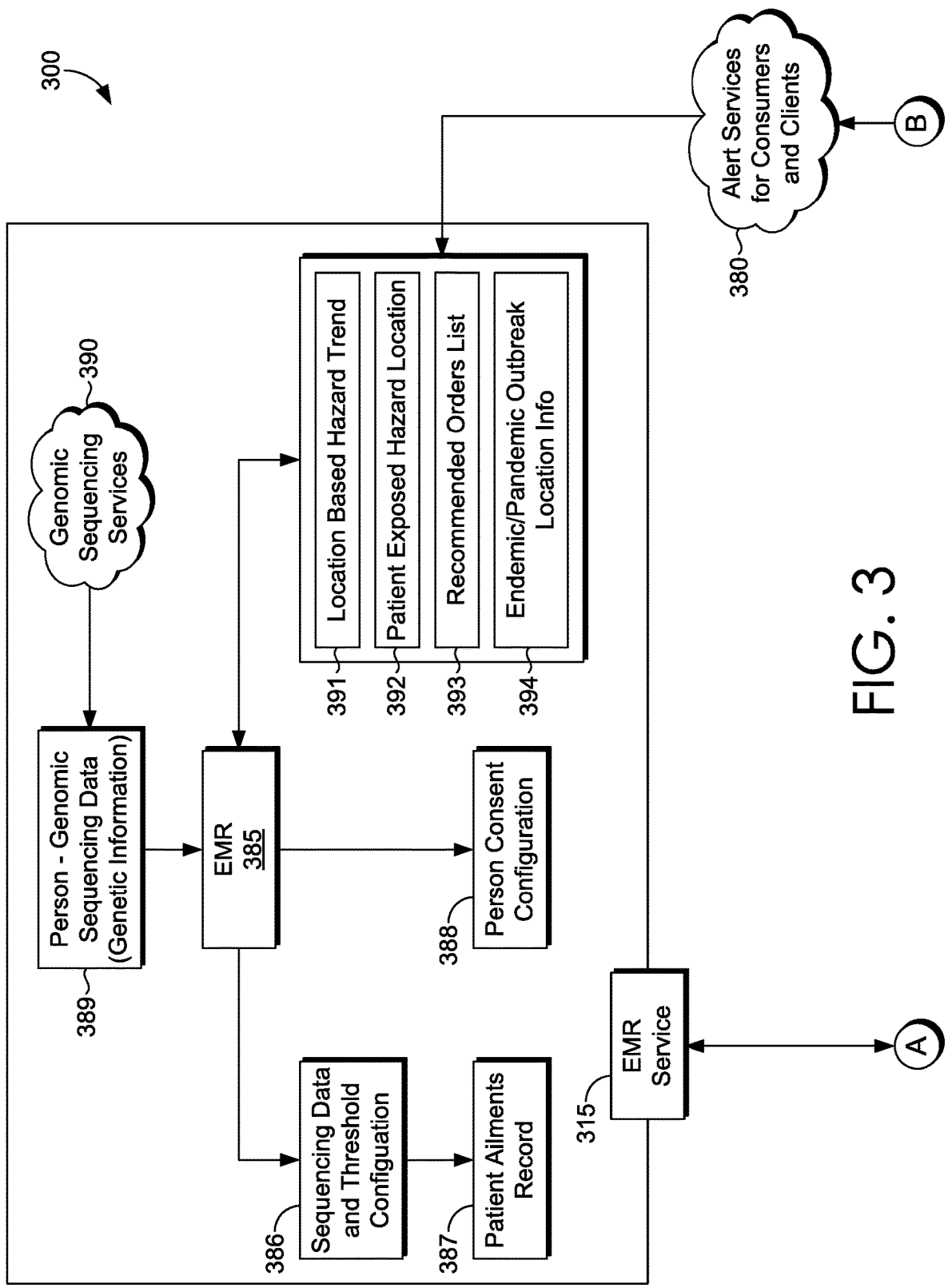

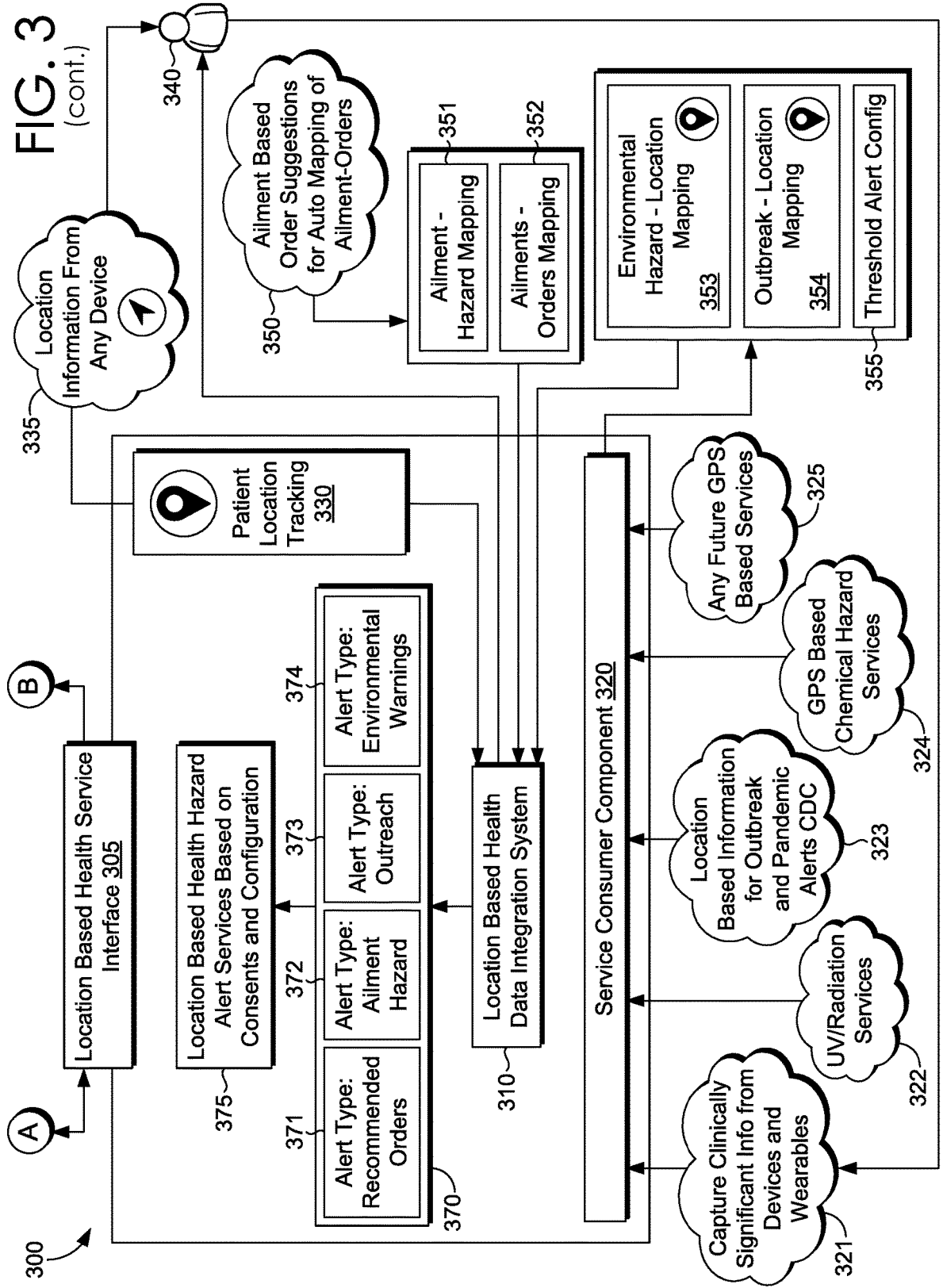

LOCATION-BASED HEALTHCARE SYSTEM

BACKGROUND

The largest drivers of healthcare cost are over diagnosis and over treatment. Patients are receiving care that is sometimes ineffective and sometimes unsafe. But the truth is that many of the tests and procedures ordered by medical practitioners are wasteful, unnecessary, and potentially harmful. A missing link in treatment or care delivery can be the cause of over diagnosis, which is both economically and physically harmful to a patient. Part of the problem is that in many cases, physicians don't feel clinically certain about what's occurring with the patient, and they're not willing to rest with that uncertainty. Thus, physicians feel that they need to do more tests and refer patients to specialists.

According to studies, environmental factors are a root cause of over diagnosis and cost—particularly in developing countries. Patient exposure to environmental or occupational hazards can set off predisposed ailments or create entirely new ailments, and is a primary concern in preventative healthcare. Environmental impacts are estimated to cause about 25% of death and disease globally, and could reach nearly 35%. It is estimated that one-fifth of the healthcare budget is being consumed by tests and procedures ordered by medical practitioners in trying to identify conditions that are set off by environmental or ecosystem interaction.

There is currently no mechanism that facilitates preventative healthcare based on patient locations to assist physicians in diagnosing the cause of a patient's conditions or ailments that may be associated with environmental factors. A location-based system that monitors exposure to certain environmental factors and assess patient risk based on medical information would assist physicians in diagnosing particular ailments and reduce inappropriate diagnostic procedures, ultimately promoting decision accuracy and diagnosis for better care delivery. Furthermore, a location-based healthcare system, by aggregating data from multiple patients in a given location, would be capable of predicting an outbreak with greater accuracy and in less time than current measures of physician communication and centralized databases.

BRIEF SUMMARY

The present application generally relates to media, systems, and methods for various embodiments of a location-based healthcare system. In one embodiment, a computerized method for improving medical records of an individual is presented. The method of this embodiment comprises: obtaining from a mobile device a location of the individual; retrieving from a record-keeping database medical-related information associated with the individual; retrieving from a service provider an environmental report for the location of the individual, wherein the environmental report comprises one or more environmental factors; determining, based on the medical-related information associated with the individual, that an exposure to the environmental factor poses a medical risk; and based on determining the medical risk, communicating instructions to the record-keeping database to store, in association with the individual, information related to the exposure to the environmental factor.

In another embodiment, a computerized method for communicating an alert to an individual of a medical-related risk is presented. In this embodiment, the method comprises: receiving a hazard report from a service provider, wherein the hazard report is associated with an area; retrieving an individual-specific location from a mobile device associated with the individual; determining that the individual-specific location is within or proximate to the area associated with the hazard report; retrieving from a record-keeping database a medical-related information associated with the individual; based at least in part on the medical-related information associated with the individual and the hazard report, determining that the area poses the medical-related risk to the individual; and communicating the alert to the individual of the medical-related risk associated with the area.

Additional objects, advantages, and novel features of the various embodiments are described below.

BRIEF DESCRIPTION OF THE DRAWINGS

The present application is described in detail below with reference to the attached drawing figures, wherein:

FIG. 3 is a block diagram of an exemplary location-based health system;

DETAILED DESCRIPTION

The subject matter of the present application is described with specificity herein to meet statutory requirements. However, the description itself is not intended to limit the scope of this patent. Rather, the claimed subject matter might also be embodied in other ways, to include different steps or combinations of steps similar to the ones described in this document, in conjunction with other present or future technologies. Moreover, although the term "step" may be used to connote different elements of methods employed, the terms should not be interpreted as implying any particular order among or between various steps unless it explicitly described that the order of the steps is critical for implementing an embodiment.

Various embodiments of the present invention are directed to methods, systems, and computer-readable media for a system and method for improving the healthcare records of a patient by storing patient location information and hazardous exposure that may be associated with medical risks. Some embodiments alert or warn a patient of a medical-related risk associated with an area. Some embodiments provide physicians or medical providers with alerts or recommendations for orders or suggested care associated with patient ailments or symptoms based on exposure to a location-specific contagion. Some embodiments provide instructions to store information related to location-specific exposure to certain environmental events on a health-records database associated with a patient. Other embodiments may determine, based on an aggregate of patient information, that a particular ailment or contagion is increasing in a particular area, and it may provide for an alert to others in the area or other entities of a potential endemic.

Figure 1:
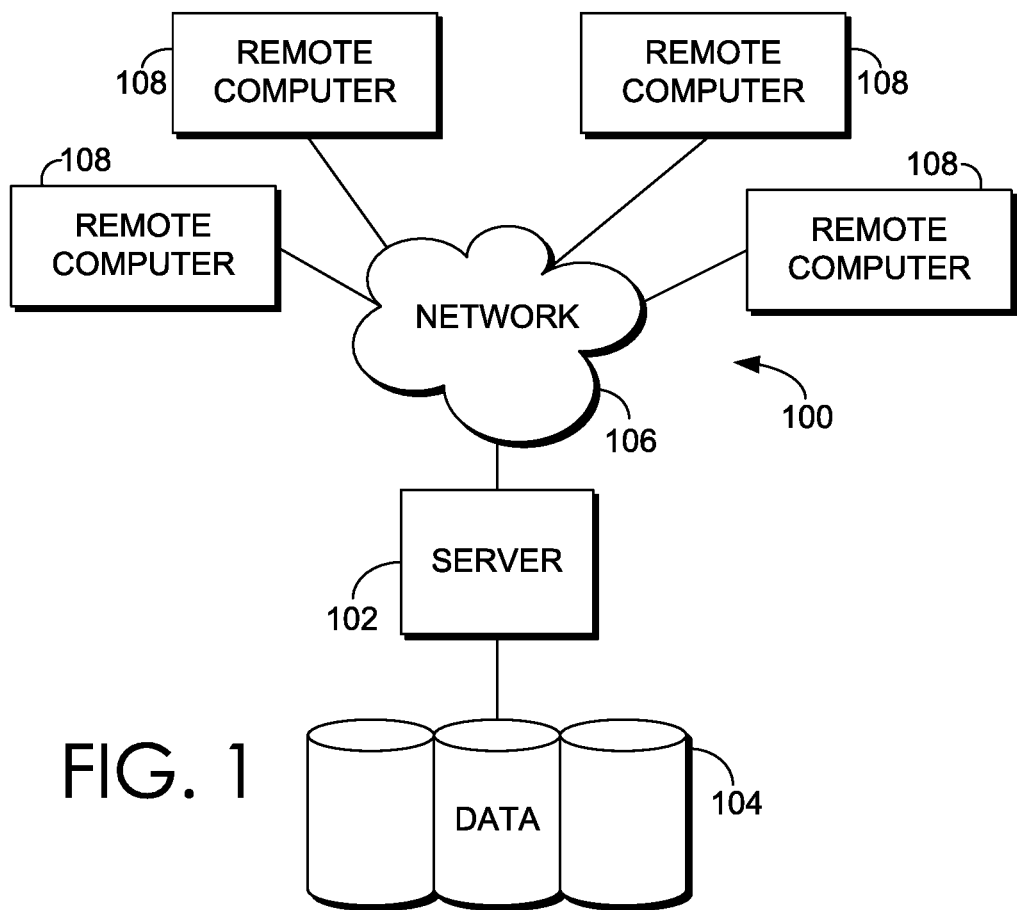
FIG. 1 is a block diagram of an exemplary computing environment suitable to implement embodiments of the various embodiments.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention is a special computing system that can leverage well-known computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a microphone (e.g., voice inputs), a touch screen, a pointing device (commonly referred to as a mouse), a trackball, or a touch pad. Other input devices comprise satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
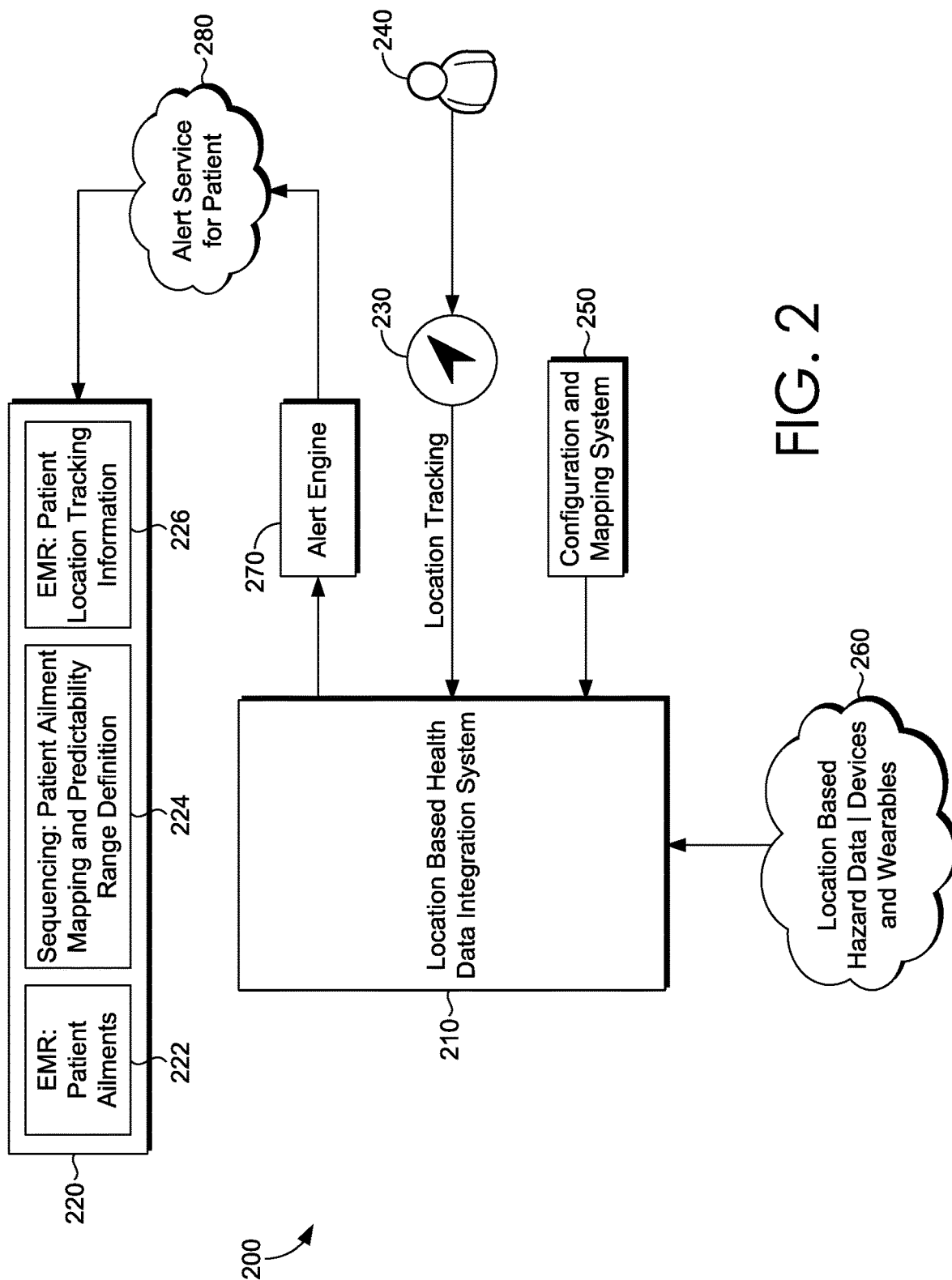
FIG. 2 is a high-level block diagram of an exemplary location-based health system.

Turning now to FIG. 2, a high-level flow chart describing one embodiment of a location-based health system 200 is presented. As shown in this embodiment, the location-based health system 200 may comprise a Location-Based Health Data Integration System (LBHDIS) 210. The LBHDIS 210 may be in communication with a location tracking device 230, which monitors the location of the patient 240. In addition, the LBHDIS 210 may also communicate with other application programming interface (API) services, devices, and wearables 260. The LBHDIS 210 may communicate with an alert engine 270. In some embodiments, the alert engine 270 uses defined rules and categories of various alerts generated from the LBHDIS 260. The alert engine 270 may communicate with an alert service 280. Both the alert service 280 and the LBHDIS 210 may communicate with an electronic medical record (EMR) system 220. The EMR system 220, in some embodiments, may comprise information associated with patient ailments 222; patient genomic sequencing, patient aliment mapping, and predictability range definition 224; and/or patient location tracking information 226.

Turning now to FIG. 3, another embodiment of a location-based health system 300 is described in further detail. This embodiment comprises a location-based health service interface 305, which comprises a number of components; notably an LBHDIS 310, a service consumer component 320, a patient location tracking component 330, an alert engine 370, and a consent-based alert service 375. The location-based health service interface 305, in some embodiments, may communicate with an EMR service 315, devices and wearable 321; $3^{rd}$ party services such as 322-325; or more generally any database or service that may provide information helpful for determining a patient's exposure to a potentially hazardous condition related to a particular location or may assist a healthcare provider in providing patient healthcare.

Beginning with the LBHDIS 310, the LBHDIS 310 may receive information associated with the location of a patient 340 from a location tracking device 335. The location tracking device 335 may be any device capable of determining and transmitting location information of the patient 340. These devices are generally known and readily available, and may include mobile phones, tablets, smart watches, etc. These devices may determine location in a number of different manners, such as Bluetooth, Infrared, GPS, etc. It should be readily known to one skilled in the art that the location tracking device 335 and the method by which it determines location is not limited to the devices stated in this application and can include future location tracking systems having the ability to communicate the location of the patient 340. Additionally, information associated with the location of the patient 340 may be communicated from the location tracking device 335 to a patient location tracking component 330. The location may be monitored on a real-time basis or may be monitored intermittently. The patient location tracking component 330 may store the location information and/or may communicate the location information to the LBHDIS 310. Alternatively, in some embodiments, the location information may be directly communicated from the location tracking device 335 to the LBHDIS 310.

A service consumer component 320 may also receive information associated with the patient location, such as clinically significant information from devices or wearables 321. The clinically significant information may be any information regarding factors that contribute to an ailment or would help a medical provider in diagnosing an ailment or provide healthcare services. Some non-limiting examples of clinically significant information could be the amount of time the patient 340 is exposed to the sun; the amount of exercise the patient 340 receives; the weight gain or weight loss of the patient 340 over time; a change in the patient's body temperature, blood pressure, heart rate; etc. This information may be gathered by wearable devices. These devices may be the same the mobile devices described above. These wearable devices may also include other devices designed to capture information about the patient 340 or the patient's 340 external environmental surroundings, including external devices, such as heart-rate monitors, blood pressure monitors, air-quality monitors, UV sensors, etc. These wearable devices are not limited to external devices as described, but may include surgically implanted devices, such as pace makers, pain pumps, insulin pumps, etc. Additionally, in some embodiments, these devices may work together to communicate information about the patient 340 to the service consumer component 320. For example, an internal insulin pump might communicate via short distance communication methods to a mobile device, which might, in turn, relay the information to the service consumer component 320 via a long distance communication method.

The service consumer component 320 may also receive information about the patient's 340 surroundings from API's, for example a third-party service, such as UV radiation services, location-based information for outbreak and pandemic alerts from the Centers for Disease Control (CDC), GPS based chemical hazard services 324, and any future GPS or location-based service 325. Other examples of APIs might include weather and new reporting services. It should be understood that the number of APIs delivering information to the service consumer component 320 can be virtually unlimited and may deliver various types of location-based information.

Once information is received, in some embodiments the service consumer component 320 may communicate to a configuration and mapping system 356, which may communicate with the LBHDIS 310. The configuration and mapping system 356 may be comprised of multiple components, such as components for ailment hazard mapping 351, ailments orders mapping 352, environmental hazard location mapping 353, outbreak location mapping 354, and threshold alert configuration module 355.

The ailments hazard mapping component 351 may be a configuration system or mapping of all the ailments and its associated environmental hazards based on information received from the service consumer component 320 or other sources, including being downloaded from medical-based information sources. For example, if a person is suffering from allergy condition such as asthma, the hazards listed for this particular ailment might be pollens, dusts, air pollutions, seasonal changes, wind, temperature, altitude, etc.

The ailments order mapping component 352 may be the module which maps lists of ailments with recommended orders list 393. The mapped data can be retrieved from cloud service 350 through analytics data gathered across multiple clinics who are interested in publishing recommended orders for given ailments. For example, if a person is arriving from a location with an endemic disease or outbreak, an associated recommended list of orders required for that particular endemic disease or outbreak may be provided.

The environmental hazard location mapping component 353 may be mapped data that contains all environmental hazards associated with a given location. This data may be gathered from datasets provided by service providers to identify hazard locations. For example, the services may include UV index level, water contamination across the given location, pollen count, noxious gases, etc. The environmental hazard location mapping component 353 may also utilize an aggregate of data across multiple patients using location history and may signal that an alert is needed for others in the same location.

The outbreak location mapping component 354 may gather data from external services available today and future services, such as the APIs, patient location tracking devices and wearables, to identify endemic disease outbreak at a given location. It may also contain additional details required for more precise clinical decisions. At a higher level this module may contain mapping of outbreak diseases associated with given location as well. In one example, information from the CDC regarding a pandemic or epidemic associated with a specific area may be communicated to the outbreak location mapping component 354. In another example, the outbreak location mapping component 354 may determine a risk of an epidemic based on an aggregate of clinically signification information from devices and wearables 321 across many patients in a particular region that may have similar changes in clinically significant information.

The threshold alert configuration module 355 may contain configuration data associated with individual hazards. The threshold value defines what level of exposure and the duration of that exposure that may constitute a hazard to the person.

Turning back now to the LBHDIS 310 part of the location-based health service interface 305, the LBHDIS 310 may communicate with an alert engine 370. The alert engine 370, may be the part of the system that comprises well-defined rules and categories of various alerts generated from LBHDIS 310. The alert engine 370 may be responsible for sending alert data to reporting services through which many entities consume services, such as person, EMR, physician, hospital, pharmacy etc. The alert engine 370 may contain further categories of information, such as, recommendation orders 371, ailment hazard 372, outbreak information 373, and/or environmental warnings 374. For example, the alert recommendation orders 371 may be the part of alert system that is responsible for gathering enough information to ensure that it provides a list of recommended orders gathered from configuration and mapping 350-355 to the EMR service 315 for accurate clinical decision support and support physician diagnosis decisions. A real-world example might be: if a person is visiting hospital after her travel to a location where an Ebola outbreak has occurred. The data will be captured by the LBHDIS 310 during the person's visit based on the location tracking of the person. Subsequently, a recommended list of orders may be generated and suggested to physician based on the person's consents.

The alert engine 370 may also contain an ailment hazard component 372. The ailment hazard component 372 may be responsible for sending alerts based on a location hazard that can trigger or aggravate the conditions within the patient 340. For example, the patient 340 may have asthma. Based on information received by APIs 322-325 and delivered to the LBHDIS 310, the pollen count of the particular location may be high enough to aggravate the symptoms of the asthmatic. Thus, an alert may be generated and communicated to the patient 340 or another, based on consents, that the pollen count is too high. In another embodiment, an alert or suggestion may communicate to the patient 340 that preventative medications should be increased to avoid having to use a rescue inhaler.

Further, the alert engine 370 may comprise an outbreak alert component 373. This component may be responsible for generating an alert to persons within a specific area that an epidemic may be associated with a particular area. The alert might suggest that persons move to another area that is not associated with the outbreak and may recommend moving to an area where the hazard has not occurred. Similarly, the alert engine 370 may contain an alert type or component for environmental warnings 374. Like the outbreak alert component 373, the environmental warning component 374 may communicate an alert based on environmental factors, such as pollens, water pollution, air pollution, noxious gas contamination, or UV exposure, or other environmental factors that may pose potential harm to a patient. The environmental warning component 374 may communicate or suggest that persons move to another area that is not associated with the environmental hazard and may recommend moving to safer area, such as indoors.

The alert engine 370 may also communicate with patient consent configurations on the consent-based alert service 375 to ensure the alert messages are sent to respective entities based on the consent configuration. For example, the patient 340 may consent to having the location information delivered to a primary care physician when the patient location is associated with an outbreak.

Turning now to the EMR service 315, which may be in communication with the location-based health service interface 305, the EMR service 315, in some embodiments, may comprise an EMR database 385. The EMR database 385 may store or be in communication with another database that stores information related to a person's consent configuration 388, sequencing data and threshold configuration 386, patient ailments data 387, genomic sequencing data 389 that may be provided by genomic sequencing services 390, and other information, such as location base hazard trends 391, patient exposed hazard location 392, recommended orders list 393, and endemic/pandemic outbreak location 394.

The sequencing data and threshold configuration 386 may provide a mechanism to get a patient's complete sequencing data and, based on the analysis, may provide predictable variants data along with threshold percentages. The medical provider or the system may help in identifying each of the predictable conditions with higher threshold, and may help to store it as part of a patient ailment record 387. The patient ailment record 387 may store information collected by the EMR service 315, including all the ailments associated with the patient 340 and hold this information for future analyses.

Similarly, the EMR database 315 may store or communicate with another database that stores the person consent configuration 388. The patient may choose to personalize the consent information so as to maintain privacy. The patient may choose to have alerts sent only to the patient, or choose to have the alerts sent to a primary care physician, or another physician of the patient's choosing. More generally, the patient may personalize how the medical information is to be distributed in any fashion. Accordingly, the patient may also consent to have their location monitored but may not allow that location information to be shared; instead, only allowing exposure information to be shared with others of the patient's choosing. Alternatively, the patient may alter the consent configurations such that information is only shared with others when exposures to hazards create a certain threshold of risk to the patient.

The EMR service 315 may also include genomic sequencing data 389. The genomic sequencing data 389 may be stored or received from a genomic sequencing service 390. The genomic sequencing data 389 may be one of various types of patient-specific information that is housed or retrieved by the EMR service 315. Patient-specific data, such as this, may be used by the location-based health service interface 305 to determine that a particular individual may be at a higher risk or predisposition to certain ailments, and may determine an alert is necessary based on information received from the service consumer component 320, the location tracking device 335 and/or the configuration and mapping system 356, described above. Once an alert is determined, the alert may be communicated via an alert service 380, which may be in communication with the location-based health service interface 305 and/or the EMR service 315. The alert may be communicated to any person or entity based on the patient consent configurations 388. These include, but are not limited to, physicians, care providers, insurers, hospitals, emergency department, etc. The location-based health service interface 305 and/or the EMR service 315 may be a computing system such as that described in FIG. 1.

Figure 4:
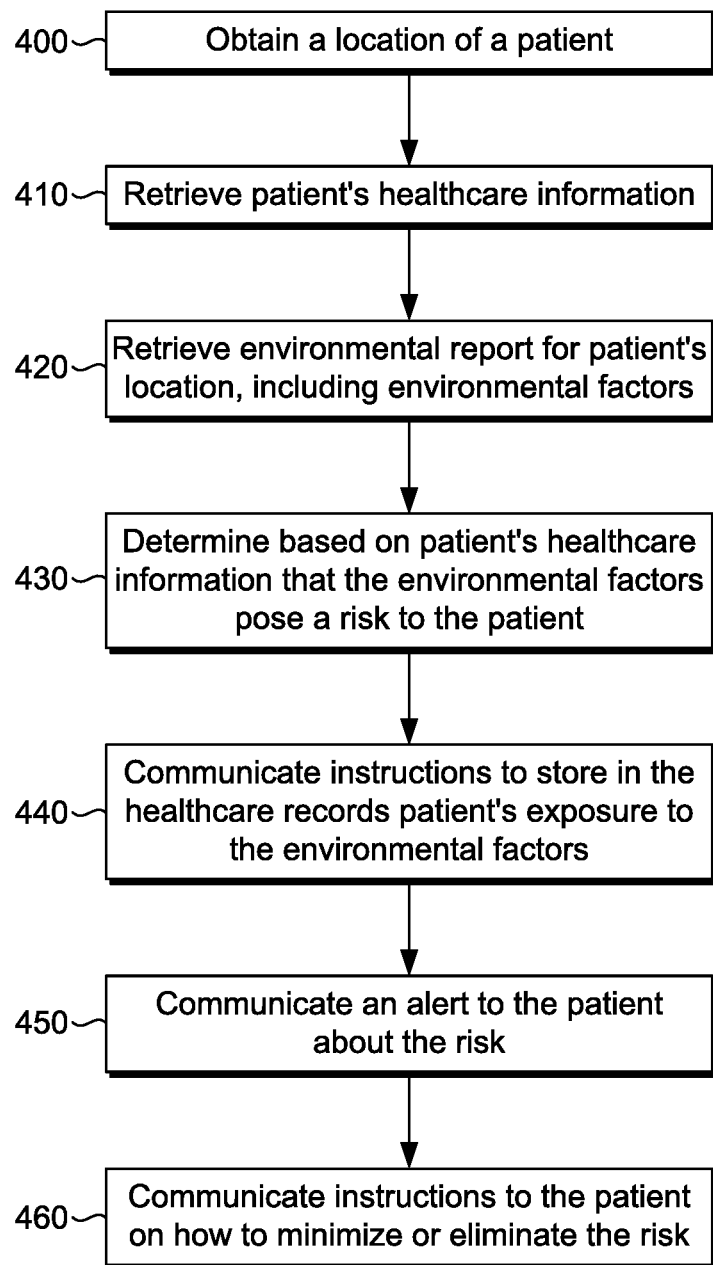
FIG. 4 is a flow chart of an exemplary method for retrieving and storing a patient's location information in association with the patient's healthcare information.

FIG. 4 depicts one embodiment of a computerized method for utilizing an embodiment of a location-based healthcare system, such as the two exemplary embodiments described in FIGS. 2-3. For example, a general computer, such as that described by the computing environment in FIG. 1, may be contain computer-executable instructions embodied that execute a method for improving medical records of an individual or patient based on location-specific risks posed to the patient. In step 400 of FIG. 4, the computer may be instructed to obtain from a mobile device the location of a patient. Alternatively, in another embodiment, the computer may receive information associated with a patient's location, which may then prompt the computer to continue with step 410.

In step 410 of the exemplary method of FIG. 4, the computer retrieves from a database, the medical records or health information of the patient. As seen in the embodiment of FIG. 3, this step may be performed when the location-based health service interface 305 retrieves the medical records or health-related information of the patient from the EMR service 315. Similarly, in step 420 of FIG. 4, the method may comprise retrieving from a service provider an environmental report for the location of the patient. The service provider may be the APIs previously discusses, e.g., a third party that may deliver reports about environmental conditions or factors, such as pollen count, UV index, city pollution reports, etc.

Step 430 of FIG. 4 may comprise determining, based on the medical records or information of the patient, that the patient's exposure to certain environmental conditions or factors at the patient's location may pose a risk to the patient. The risk may be the type of risk that would affect all persons in the area, such as a viral outbreak. Alternatively, it may pose a patient-specific risk, such as a UV index that is too high for a patient currently undergoing chemotherapy to be outside for an extended amount of time. In some embodiments, a patient-specific risk may be predefined in the medical records. In other embodiments, the patient-specific risk may be determined by a location-based service interface that associates certain diagnoses with certain risks, such as determining from the medical records that a patient has asthma and associated a risk of exposure to a particular environmental pollen level.

Under step 440, the medical records for the patient may be improved by having the location-based service interface communicate with the EMR service that a patient has been exposed to a patient specific risk, such as that determined by step 430, and instructing the EMR service to store the information associated with the patient for future access, e.g., by a physician, a hospital, an insurance company, or the patient.

In some embodiments an additional step of communicating an alert to the patient may be provided, such as step 450 of FIG. 4. The alert may be in any form that signals to the patient that a patient-specific risk might be present. Some examples of alerts might include text messages, emails, phone calls, social media status changes, etc. Additionally, the alert may also be provided to other entities, such as hospitals in the surrounding area, primary care physicians, first-responder authorities, patient-specified emergency contacts, etc. The patient may preselect the desired recipients of alerts and this data may be stored in a component of an alert engine associated with an embodiment of a location-based health service interface.

In other embodiments, the alert may communicate a suggestion or instructions to the patient, such as the represented by step 460 of FIG. 4. The instructions communicated to the patient may be instructions to reduce or eliminate the patient-specific risk. For example, it may be determined that a patient with sensitivity to UV radiation is outdoors. A certain amount of UV radiation exposure to the patient may not be harmful; however, after a certain threshold is reached, the patient may suffer negative effects from the exposure. Having determined, such as from an API described previously, the level or index of UV radiation for a given area, a location-based health service interface, or a component of the location-based health service interface, may determine the amount of time the patient may spend outdoors in a certain area before reaching the threshold level of sun exposure that is safe for the patient. Once the patient reaches the threshold level, the system may send an alert with instructions to move from the outdoor location to an indoor location where UV exposure would be reduced or eliminated.

Figure 5:
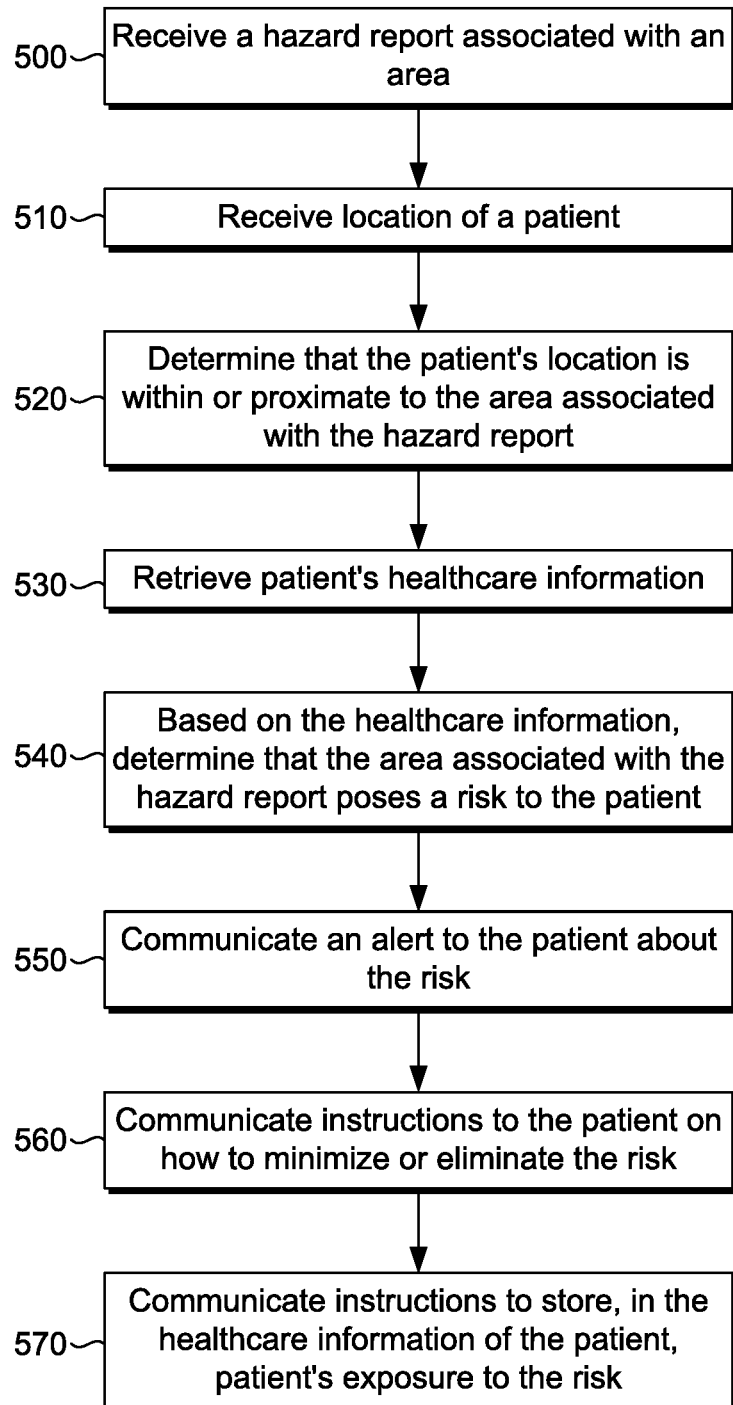
FIG. 5 is a flow chart of an exemplary method for communicating an alert to a patient based on a location-specific risk to the patient.

In another embodiment, the computerized method performed by a location-based health service interface may be similar to that described by FIG. 5. In step 500, the location-based health service interface may receive a hazard report associated with an area. For example, the hazard report may be received from an API, as described above. The hazard report may be associated with any environmental hazard, occupational hazard, or man-made hazard that may pose a health threat to persons in the area. For example, the hazard may be an allergen, a dangerous ultraviolet index, a dangerous air pollution index, a bacterial outbreak, a viral outbreak, a fungal outbreak, an algal bloom, a chemical spill, a contaminated water alert, a radiation or radioactivity increase, and so on. A hazard report may be associated with any activity or event that may pose a threat to human health or safety, whether the activity affects all persons in the area or whether the activity increases the health risks of only persons in the area with sensitivity to a particular hazard or activity.

In step 510, the health service interface may receive a location of a patient. As described above in greater detail, the location of a patient may be sent to the interface from a mobile device capable of determining location. Additionally, the interface may receive health information related to the patient's measureable outcome data from patient wearables, such as heart rate, oxygen stats, blood pressure, sugar level, etc.

In step 520 of the exemplary method, the health service interface may determine that the patient's location is within or is proximate to the area associated with the hazard report or event. For example, if the interface receives a report that a certain geographical county is experiencing a hazard associated with an oil or chemical spill, this could be hazardous to patients that are exposed. The interface may determine that certain patients are located within the county experiencing the hazard and may also determine that other patients are located within counties surrounding the county experiencing the hazard. In other embodiments, it may determine that patients are within a certain distance surrounding the hazard location. In yet other embodiments, the location distances for determining what patients are proximate to the hazardous event may be predefined based on the type of hazard, or may be determined by the integration system as aggregate data of multiple patients is received, such as detecting the spread of a contagion.

In step 530, the interface may retrieve the healthcare records associated with the patients that are within or proximate to the area associated with the hazard. The healthcare records may be retrieved from an EMR system.

In step 540, the interface may determine that the hazard poses a health-related or medical-related risk to the patients within or proximate to the area. For example, the hazard associated with the area may be an abnormally high pollen count. Based on the health records of the patients in or around the area, the interface may determine that patients with, for example, a diagnosis of asthma; a history of lung conditions or cancer; or temporarily conditions, such as the flu or bronchitis, are at risk of aggravating their individual ailments.

Based on determining that a patient might suffer a health-related risk, the interface, via an alert engine, might send an alert notification to a patient. The alert may be in any form that communicates to the patient that they might be exposed to a hazard posing a health-related risk or they might have the potential to be exposed to a hazard posing a health-related risk if they enter a certain area.

In some embodiments, the method may also comprise step 560, communicating instructions to the patient on how to reduce or eliminate the risk. For example, patients suffering from allergies might be exposed to a pollen count that breaches the safety threshold for that particular patient. The system may be able to, based on the healthcare records, suggest the patient increase preventative medication in order to reduce the chance of a server allergic reaction that may require the use of a rescue inhaler or medical care.

In some embodiments, the method may also comprise communicating instructions to an EMR system to store information about the patient's location and exposure to health risks. The information may be associated with the patient in the patient's electronic medical record so that it may later be accessed by other entities, such as a primary care physician, an emergency department of a hospital, an insurance company, etc.

In some embodiments, the system might recommend to a physician specific orders for a particular patient based on the patient's location and the patient's exposure to a health-related risk. For example, a patient might be suffering from a location-based, health-related risk that causes the patient not to be able to communicate symptoms to an emergency department physician. The physician may be able to access the medical records of the patient and determine that the patient was at a particular location and exposed to a particular risk. The interface may associate certain treatments with the risk. The interface may recommend orders associated with the treatments to the physician. A real-world example might be determining that a patient was in an area associated with an epidemic or outbreak of a particular contagion. The interface may provide information to a treating medical provider that the patient was in the area associate with a contagion. It may further recommend orders for the treatments associated with the contagion. Even if the patient was not able to communicate to the provider, maybe because of unconsciousness, their location information, the interface may be able to communicate this for them as it would have stored this information on the EMR database or system.

From the foregoing, it will be seen that this disclosure is well adapted to attain all the ends and objects described above with other advantages that are obvious and inherent to the structure.

It will be understood that certain features and subcombinations are of utility and may be employed without reference to other features and subcombinations. This is contemplated by and is within the scope of the claims.

Since many possible embodiments may be made of the without departing from the scope, it is to be understood that all matter in this application is to be interpreted as illustrative and not in a limiting sense.

What is claimed is:

1. One or more computer storage media having computer-executable instructions embodied thereon that, when executed, perform a method for improving medical records of an individual based on location-specific risks, the method comprising:
   obtaining from a mobile device a location of the individual;
   retrieving from a record-keeping database a medical-related information comprising a predisposition unique to the individual to certain ailments linked with an environmental factor associated with the individual, wherein the retrieving of medical-related information is prompted by the obtaining of the location of the individual by the one or more computer storage media;
   retrieving from a service provider an environmental report for the location of the individual, wherein the environmental report further comprises one or more of the environmental factor;
   determining, at a device, based on the medical-related information and the environmental factor, that an exposure to the environmental factor at the location of the individual exceeds a safety threshold posing a medical risk to the individual based on the predisposition unique to the individual linked with the environmental factor; and
   automatically initiating, at a device, a medical order in the record-keeping database for the individual related to the exposure to the environmental factor based on determining the exposure to the environmental factor at the location of the individual exceeds the safety threshold posing a medical risk to the individual based on the predisposition unique to the individual.

2. The media of claim 1, wherein the method further comprises the step of communicating, to a medical provider, information associated with exposure of the individual to the environmental factor.

3. The media of claim 2, wherein the method further comprises the step of recommending, to the medical provider, orders for the individual based on exposure of the individual to the environmental factors and based on one or more stored consent configurations associated with the individual.

4. The media of claim 1, wherein the record-keeping database is an electronic medical record (EMR) system.

5. A computerized method for communicating an alert to an individual of a medical-related risk, the method comprising:
receiving a hazard report from a service provider, wherein the hazard report is associated with an area;
retrieving an individual-specific location from a mobile device associated with the individual;
determining that the individual-specific location is within or proximate to the area associated with the hazard report;
retrieving from a record-keeping database a medical-related information comprising a predisposition unique to the individual to certain ailments linked with an environmental factor associated with the individual;
based at least in part on the medical-related information associated with the individual and the hazard report, determining that the area poses the medical-related risk to the individual based on the predisposition unique to the individual linked with the environmental factor;
retrieving a threshold configuration for the individual;
determining, at a device, based on the area, the threshold configuration, and the individual-specific location, that the individual was exposed to the medical-related risk above a threshold; and
automatically initiating, at a device, a medical order in the record-keeping database for the individual related to the exposure to the environmental factor based on determining that the individual was exposed to the medical-related risk at the individual-specific location based on the predisposition unique to the individual above the threshold.

6. The method of claim 5, wherein the medical-related risk is at least one of an allergen, a dangerous ultraviolet index, a dangerous air pollution index, a bacterial outbreak, a viral outbreak, a fungal outbreak, and an algal bloom.

7. The method of claim 5, further comprising the step of communicating to the record-keeping database instructions to store, in association with the individual, information related to exposure to the medical-related risk.

8. The method of claim 7, wherein the method further comprises the step of communicating, to a medical provider, information related to exposure of the individual to the medical-related risk.

9. The method of claim 8 further comprising the step of providing a recommendation, to the medical provider, orders for the individual based on exposure of the individual to the medical-related risk and the predisposition unique to the individual.

10. The method of claim 5, further comprising the step of providing a suggestion to the individual.

11. The method of claim 10, wherein the suggestion comprises instructions to move from a first location to a second location, and wherein the second location reduces or eliminates exposure of the individual to the medical-related risk.

12. A computerized system comprising:
a mobile device configured to monitor location of an individual;
one or more processors; and
computer storage memory having computer-executable instructions stored thereon which, when executed by the processor, implement a method for tracking exposure of the individual to environmental events that create a medical-related risk to the individual, the method comprising:
receiving a hazard report from a service provider, wherein the hazard report is associated with an area and an environmental factor;
retrieving in approximately real-time an individual-specific location from the mobile device associated with the individual;
determining that the individual-specific location is within or proximate to the area associated with the hazard report;
retrieving from a record-keeping database medical-related information comprising a predisposition unique to the individual to certain ailments linked with the environmental factor associated with the individual;
based at least in part on the medical-related information associated with the individual and the hazard report, determining, at a device, that the environmental factor at the location of the individual exceeds a safety threshold and poses the medical-related risk to the individual based on the predisposition unique to the individual linked with the environmental factor; and
automatically initiating, at a device, a medical order in the record-keeping database for the individual-related to the exposure to the environmental factor at the location of the individual when the exposure to the environmental factor at the location of the individual exceeds the safety threshold posing a medical risk based on the predisposition unique to the individual.

13. The method of claim 12, further comprising the step of providing a suggestion to the individual, wherein the suggestion comprises instructions for the individual to begin or alter a preventative medication.

14. The method of claim 12, further comprising the step of determining, based on the area and the individual-specific location, that the individual was exposed to the medical-related risk.

15. The method of claim 12, further comprising the step of communicating to the record-keeping database instructions to store, in association with the individual, information related to exposure to the medical-related risk.

16. The method of claim 15, wherein the method further comprises the step of communicating, to a medical provider, information related to exposure of the individual to the medical-related risk.

17. The method of claim 16 further comprising the step of recommending, to the medical provider, orders for the individual based on exposure of the individual to the medical-related risk.

18. The method of claim 17, further comprising the step of providing a suggestion to the individual, wherein the suggestion comprises instructions to move from a first location to a second location, and wherein the second location reduces or eliminates exposure of the individual to the medical-related risk.

19. The one or more computer storage media of claim 1, wherein the predisposition to certain ailments comprises previous and current diagnosis for the individual.

* * * * *

UNITED STATES PATENT AND TRADEMARK OFFICE
CERTIFICATE OF CORRECTION

PATENT NO. : 11,450,416 B2
APPLICATION NO. : 15/391552
DATED : September 20, 2022
INVENTOR(S) : Satya Krishna Pillarisetty et al.

It is certified that error appears in the above-identified patent and that said Letters Patent is hereby corrected as shown below:

On the Title Page

On Page 2, under OTHER PUBLICATIONS Line 4:
Delete "10pages." and insert -- 10 pages. --.

In the Drawings

Sheet 3 of 6, Fig. 3, Reference Numeral 386:
Delete "Configuation" and insert -- Configuration --.

In the Specification

Column 3, Line 47:
Delete "Video Electronic Standards Association (VESA)" and insert -- Video Electronics Standards Association (VESA) --.

Column 11, Line 2:
Delete "measureable" and insert -- measurable --.

In the Claims

Claim 13, Column 14, Line 35:
The line reading "The method of claim 12, further comprising the step" should read -- The computerized system of claim 12, further comprising the step --.

Claim 14, Column 14, Line 39:
The line reading "The method of claim 12, further comprising the step" should read -- The computerized system of claim 12, further comprising the step --.

Signed and Sealed this
Thirteenth Day of December, 2022

Katherine Kelly Vidal
*Director of the United States Patent and Trademark Office*

CERTIFICATE OF CORRECTION (continued)
U.S. Pat. No. 11,450,416 B2

Claim 15, Column 14, Line 43:
The line reading "The method of claim 12, further comprising the step" should read -- The computerized system of claim 12, further comprising the step --.

Claim 16, Column 14, Line 47:
The line reading "The method of claim 15, wherein the method further" should read -- The computerized system of claim 15, wherein the method further --.

Claim 17, Column 14, Line 51:
The line reading "The method of claim 16, further comprising the step of" should read -- The computerized system of claim 16, further comprising the step of --.

Claim 18, Column 14, Line 55:
The line reading "The method of claim 17, further comprising the step" should read -- The computerized system of claim 17, further comprising the step --.